United States Patent
Shaikh et al.

(10) Patent No.: US 12,322,499 B2
(45) Date of Patent: Jun. 3, 2025

(54) ORDER SELECTION AND ENTRY MANAGEMENT SYSTEM

(71) Applicant: CERNER INNOVATION, INC., Kansas City, KS (US)

(72) Inventors: Imran Abdul Majeed Shaikh, Yellapur (IN); Prashant Pagi, Karnataka (IN); Kiran Chornoor Raghunathachar, Bangalore (IN)

(73) Assignee: Cerner Innovation, Inc., Kansas City, MO (US)

(*) Notice: Subject to any disclaimer, the term of this patent is extended or adjusted under 35 U.S.C. 154(b) by 1335 days.

(21) Appl. No.: 15/782,623

(22) Filed: Oct. 12, 2017

(65) Prior Publication Data
US 2019/0114394 A1  Apr. 18, 2019

(51) Int. Cl.
| | |
|---|---|
| *G16H 40/20* | (2018.01) |
| *G06F 3/0482* | (2013.01) |
| *G06F 16/435* | (2019.01) |
| *G16H 10/60* | (2018.01) |
| *G16H 50/20* | (2018.01) |

(52) U.S. Cl.
CPC .......... *G16H 40/20* (2018.01); *G06F 3/0482* (2013.01); *G06F 16/435* (2019.01); *G16H 10/60* (2018.01); *G16H 50/20* (2018.01)

(58) Field of Classification Search
CPC ........ G06Q 50/22; G06Q 50/24; G06F 19/30; G06F 19/32; G06F 19/325; G06F 19/34; G06F 19/3456; G06F 19/3475; G06F 16/435; G06F 3/0482; G16H 10/00; G16H 10/60; G16H 15/00; G16H 20/00; G16H 20/10; G16H 20/30; G16H 20/40; G16H 20/60; G16H 20/70; G16H 20/90;
(Continued)

(56) References Cited

U.S. PATENT DOCUMENTS

| | | | | |
|---|---|---|---|---|
| 4,667,292 | A * | 5/1987 | Mohlenbrock | G06Q 10/10 705/2 |
| 7,533,353 | B2 * | 5/2009 | Dvorak | G16H 40/63 715/708 |

(Continued)

OTHER PUBLICATIONS

CPOE, Computerized Provider Order Entry, Superuser Reference Manual, MCG Health, Inc., Sep. 26, 2008, 118 pages.*
(Continued)

*Primary Examiner* — Jason S Tiedeman
(74) *Attorney, Agent, or Firm* — Invoke

(57) ABSTRACT

Computerized systems and methods facilitate inputting orders into an electronic order management system based on diagnoses entered into patient care applications. In accordance with the technology described herein, a diagnosis is received via a user interface provided by a patient care application. A type of order for the diagnosis is determined from a data store mapping each of a number of diagnoses to one or more types of orders available for entry to the electronic order management system. An order entry user interface for submitting orders to the electronic order management system is launched, and an order corresponding to the type of order identified for the diagnosis is input into the order entry user interface. The order can be reviewed by a clinician and submitted via the electronic order management system for processing and fulfillment.

18 Claims, 7 Drawing Sheets

(58) Field of Classification Search
CPC ........ G16H 50/00; G16H 50/20; G16H 50/30; G16H 50/50; G16H 50/70; G16H 50/80
USPC ........................................................ 705/2, 3
See application file for complete search history.

(56) References Cited

U.S. PATENT DOCUMENTS

| | | | | |
|---|---|---|---|---|
| 2002/0072934 | A1* | 6/2002 | Ross | G16H 40/20 705/2 |
| 2002/0147616 | A1* | 10/2002 | Pollard | G06F 19/325 705/3 |
| 2003/0225595 | A1* | 12/2003 | Helmus | G06Q 40/08 705/2 |
| 2006/0149416 | A1* | 7/2006 | Mohapatra | G16H 20/10 700/242 |
| 2007/0083805 | A1* | 4/2007 | Randazzo | G06F 40/174 715/234 |
| 2007/0168223 | A1* | 7/2007 | Fors | G06F 19/324 705/2 |
| 2007/0179807 | A1* | 8/2007 | Nessinger | G16H 10/60 600/300 |
| 2007/0265882 | A1* | 11/2007 | Jennings | G06Q 10/1095 705/7.19 |
| 2008/0027755 | A1* | 1/2008 | Portnoy | G16H 50/20 705/2 |
| 2008/0046292 | A1* | 2/2008 | Myers | G06F 16/283 705/3 |
| 2009/0018862 | A1* | 1/2009 | Sanger | G06Q 10/00 705/2 |
| 2009/0192800 | A1* | 7/2009 | Brandt | G10L 15/22 704/270.1 |
| 2010/0010833 | A1* | 1/2010 | Langdon | G16H 40/67 705/3 |
| 2011/0173029 | A1* | 7/2011 | Hanov | G16H 70/20 705/3 |
| 2012/0065997 | A1* | 3/2012 | Farooq | G16H 20/10 705/3 |
| 2013/0080190 | A1* | 3/2013 | Mansour | G06Q 10/10 705/3 |
| 2013/0246098 | A1* | 9/2013 | Habboush | G06F 40/30 705/3 |
| 2014/0200921 | A1* | 7/2014 | Hamill | G16H 10/60 705/3 |
| 2015/0039333 | A1* | 2/2015 | de Traversay | G06Q 10/0635 705/2 |
| 2015/0227689 | A1* | 8/2015 | Taylor | G16H 50/20 705/3 |
| 2015/0278457 | A1* | 10/2015 | De la Torre | G16H 50/20 705/3 |
| 2015/0332001 | A1* | 11/2015 | Goldfein | G06Q 30/04 705/3 |
| 2016/0092401 | A1* | 3/2016 | O'Connor | G06F 17/211 715/256 |
| 2017/0103175 | A1* | 4/2017 | Chopra | G16H 40/63 |
| 2017/0109341 | A1* | 4/2017 | Issa | G06F 9/451 |

OTHER PUBLICATIONS

Providers Course 1 Participant Guide Computerized Provider Order Entry (CPOE), Carolinas HealthCare System, Canopy Electronic Medical Records, Jun. 2012, 97 pages (Year: 2012).*

* cited by examiner

TRACKING LIST 400

| NAME | ACUITY | PRE-AR | REASON FOR VISIT | ETA | ARRIVAL TI | MEDICAL R | ADDMITTI | ATTENDIN |
|---|---|---|---|---|---|---|---|---|
| ADAMS, JANE | | ☐ | | | 14/11/2014 3:02 | 00002222 | | |
| BUSH, JIM | | ☐ | | | 14/11/2014 3:31 | 00001199 | | |
| DOE, JOE | | ☐ | 1:COUGH | | 19/11/2014 4:32 | 00002017 | | |
| SMITH, TOM | | ☐ | | | 25/11/2014 2:01 | 00002077 | | |
| YALE, ABBY | | ☐ | 1:MITTELSCH | | 25/11/2014 2:06 | 00002250 | | |
| ZECK, ALEX | | ☐ | | | 25/11/2014 2:12 | 00002075 | | |

402 · 404

☐ FULL SCREEN   🖨 PRINT   ↻ AGO

| RESIDENT | CURRENT L | BIRTH DAT | SEX/AGE | TEAM | PERSON ID | ENCOUNTER | TRACKING | IV STOP TI | AL |
|---|---|---|---|---|---|---|---|---|---|
| | EDWR | 09/12/1945 | 71 YEARS | | 2277000 | 2653890 | 3570769 | | PO |
| | EDWR | 05/06/1944 | 73 YEARS | | 1717171 | 0070070 | 3930390 | 🕛 | DO |
| | EDWR | 18/09/1967 | 49 YEARS | | 7722000 | 2659038 | 3570769 | 🕛 | |
| | EDWR | 10/10/1981 | 35 YEARS | | 2500000 | 2622222 | 3598765 | | PO |
| | EDWR | 20/07/1984 | 33 YEARS | | 2273574 | 2657412 | 3585296 | | DO |
| | EDWR | 12/09/1986 | 30 YEARS | | 2587878 | 2620022 | 3599865 | | DO |

YALE, ABBY  DOB:7/20/1984  AGE:33 YEARS  DOSE WT:  SEX: FEMALE  ATTENDING:REDDY, PRADEEP
ALLERGIES: NO KNOWN MEDICATION ALLERGIES  ISOLATION:  EMERGENCY FIN:000003000 [ADMIT DT: 11/24/2014 2:36 PM  MRNI00002270
DISCH DT: <NO – DISCHARGE DATE>] LOC: ED

TEMPLATES: EDSTANDARDSPATIEN...

- ✓ ☑ DIAGNOSIS
  - ☑ N94.0 MITTELSCHMERZ
- ✓ ☑ ORTERS/RX
  - ☐ XR ABDOMEN 2 VIEW – STAT
  - ☐ CROFELEMER
  - ☐ BLOOD TYPE ABO/RH
- FOLLOW-UP
- ✓ IV STOP TIMES
- NURSING DISCHARGE SUMMARY ✓
- NURSING ADMISSION SUMMARY ✓
- NURSING TRANSFER SUMMARY ✓
- VALUABLES/BELONGINGS ✓
- ED ASSISTANCE SUMMARY ✓
- ED VITAL SIGNS/PAIN ✓
- ED CHARGING
- PATIENT CHART ✓
- PRINT CHART
- ADMIT
- DISCHARGE ✓

602

| PATIENT | CLINICAL |

NAME: YALE, ABBY  CURRENT DATE: 7/26/2017 7:20:39 PM
AMERICA/CHICAGO
DOB: 7/20/1984  MRN: 00002270  FIN: 000003097
DIAGNOSIS: MITTELSCHMERZ

VISIT DATE: 11/25/2014 2:06:00 AM AMERICA/CHICAGO
ADDRESS:
PHONE:

PRIMARY CARE PROVIDER:
  NAME:
  PHONE:

EMERGENCY DEPARTMENT PROVIDERS:

MEDICAL CENTER WOULD LIKE TO THANK YOU FOR ALLOWING US TO ASSIST YOU WITH
YOUR HEALTHCARE NEEDS. THE FOLLOWING INSTRUCTIONS INCLUDE PATIENT EDUCATION
MATERIALS AND INFORMATION REGARDING YOUR INJURY/ILLNESS.

COMMENT:

YALE, ABBY HAS BEEN GIVEN THE FOLLOWING LIST OF FOLLOW-UP INSTRUCTIONS,
PRESCRIPTIONS, AND PATINET EDUCATION MATERIALS:

ALLERGIES: NO KNOWN MEDICATION ALLERGIES

MEDICATION INFORMTION.

MEDICAL CENTER ED PHYSICIANS PROVIDED YO WITH A COMPLETE LIST OF MEDICATIONS
POST DISCHARGE. IF YOU HAVE BEEN INSTRUCTED TO STOP TAKING A MEDICATION, PLEASE
ENSURE YOU ALSO FOLLOW UP WITH THIS INFORMATION TO YOUR PRIMARY CARE
PHYSICIAN, UNLESS OTHERWISE

☐ PATIENT REQUESTED ELECTRONIC DISCHARGE SUMMARY
☐ PATIENT RECEIVED ELECTRONIC DISCHARGE SUMMARY

ORDER SELECTION AND ENTRY MANAGEMENT SYSTEM

BACKGROUND

Providers of healthcare services, such as clinicians, prescribe or recommend various orders to treat ailments or conditions diagnosed in patients. An "order" is a request for one or more actions to be performed by healthcare personnel. The orders may include, for instance, medications, medical equipment or supplies, laboratory tests, or medical services, examples of which include imaging diagnostics or surgical procedures, or other appropriate treatments, procedures or therapies.

Increasingly, clinicians are utilizing electronic order management systems to enter and manage orders for their patients. One example of such an electronic order management system is the POWERORDERS application available from Cerner Corporation of North Kansas City, Mo. For instance, using such an order management system, a physician or other clinician wishing to prescribe a medication for a particular patient may initiate an order for the medication, entering details for the medication order. After initiating the order, the clinician may "sign" the order, indicating to the order management system to process the order. These electronic order management systems have advanced the state of the art well beyond and provide many efficiencies over traditional ordering methods where a clinician writes out a hardcopy of the order. With electronic order management systems, orders may be quickly transmitted to an entity that can fulfill the order, such as a pharmacy or laboratory department. Additionally, previous orders for one or more patients may be recalled by clinicians having access to a healthcare network connected with the electronic order management system, such orders being stored, for instance, in patient-specific electronic health or medical records. This allows clinicians remote from the patient, or remote from other clinicians that have placed orders, to review the ordering history for the patient.

BRIEF SUMMARY

Embodiments of the present invention generally relate to computerized systems and methods that facilitate inputting orders into an electronic order management system based on diagnoses entered into patient care applications. In accordance with the technology described herein, a diagnosis is received via a user interface provided by a patient care application. A type of order for the diagnosis is determined from a data store mapping each of a number of diagnoses to one or more types of orders available for entry to the electronic order management system. An order entry user interface for submitting orders to the electronic order management system is launched, and an order corresponding to the type of order identified for the diagnosis is input into the order entry user interface. The order can be reviewed by a clinician and submitted via the electronic order management system for processing and fulfillment.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE SEVERAL VIEWS OF THE DRAWINGS

The present invention is described in detail below with reference to the attached drawing figures, wherein:

FIG. 4 is a screenshot showing entry of a diagnosis into a user interface of a patient care application in accordance with an embodiment of the present invention;

FIG. 5 is a screenshot showing entry of an order into a user interface for submitting an order based on a diagnosis entered into a patient care application in accordance with another embodiment of the present invention;

FIG. 6 is another screenshot showing entry of an order into a user interface for submitting an order based on a diagnosis entered into a patient care application in accordance with another embodiment of the present invention.

DETAILED DESCRIPTION

Figure 1:
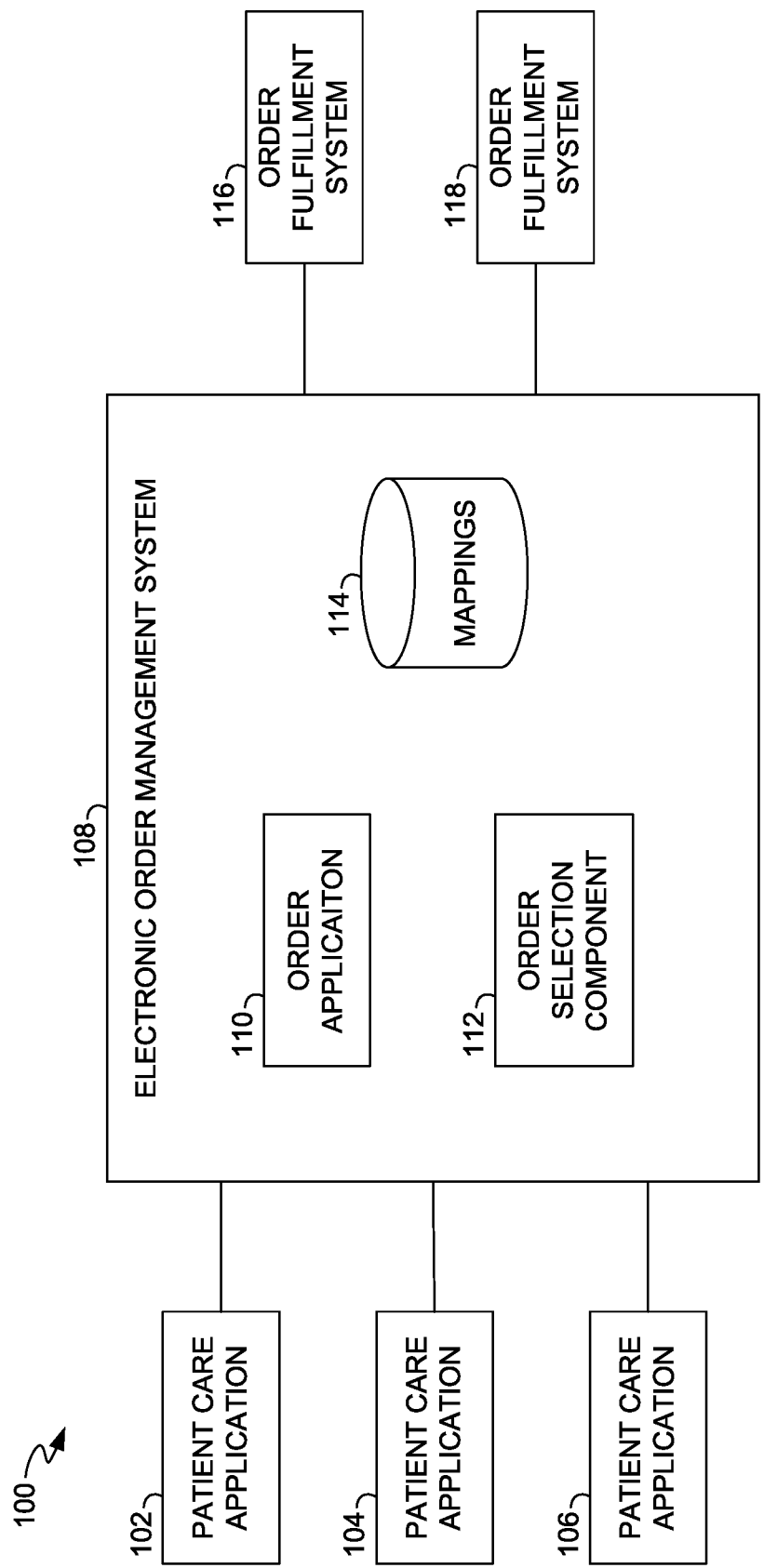
FIG. 1 is a block diagram of an exemplary system architecture in which embodiments of the invention may be employed.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

While electronic order management systems provide many advantages and efficiencies over traditional ordering methods, some drawbacks are present in current solutions. For instance, the computer system for a healthcare facility often includes a number of different patient care applications for various domains within the healthcare facility. As specific examples, an emergency care department, pediatric department, and oncology department may each have its own specialized application. While each of these patient care applications may interface with an electronic order management system, this interface is not seamless. When a clinician is working within a patient care application and needs to enter an order, the clinician must launch an order application that presents an order entry user interface separate from the user interface from the patient care application. The clinician must then manually enter the order into the order entry user interface. This process is subject to error as context is lost when switching between the two user interfaces.

Embodiments of the present technology address the technical challenge of interfacing patient care applications with electronic order management systems. Generally, embodiments are directed to computerized methods and systems that facilitate inputting orders into an electronic order management system based on diagnoses entered into patient care applications. As used herein, a "diagnosis" includes any problem, complaint, physical symptom, or illness indicated for a patient or an identification of the source of any such problem, complaint, physical symptom, or illness. In accordance with the technology described herein, a diagnosis is received via a user interface provided by a patient care application. A type of order for the diagnosis is determined from a data store mapping each of a number of diagnoses to one or more types of orders available for entry to the electronic order management system. In some configurations, globally unique diagnoses codes are used to identify diagnoses in the data store. Using such globally unique diagnoses codes allows any number of diverse patient care applications to interface with the electronic order management system for the automatic selection an entry of orders for diagnoses. An order entry user interface for submitting orders to the electronic order management system is launched, and an order corresponding to the type of order identified for the diagnosis is input into the order entry user interface. The order can be reviewed by a clinician and submitted via the electronic order management system for processing and fulfillment.

Accordingly, aspects of the technology described herein provide, among other things, a process of entering orders into an electronic order management system that is initiated from separate patient care applications in an integrated fashion so that human input and other errors may be reduced. At the same time, adherence to clinical best practices and other guidelines may be increased, resulting in fewer erroneous orders. This provides a more seamless integration between disparate patient care applications and an electronic order management system that was previously not available.

Referring to the drawings in general, and initially to FIG. 1, a block diagram is provided illustrating an exemplary system 100 in which some embodiments of the present invention may be employed. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory.

It should be understood that the system 100 shown in FIG. 1 is an example of one suitable computing system architecture. Each of the components shown in FIG. 1 may be implemented via any type of computing device. The components may communicate with each other via a network may include, without limitation, one or more local area networks (LANs) and/or wide area networks (WANs). Such networking environments are commonplace in offices, enterprise-wide computer networks, intranets, and the Internet. It should be understood that any number of the components shown in FIG. 1 may be employed within the system 100 within the scope of the present invention. Each may be implemented via a single device or multiple devices cooperating in a distributed environment. Additionally, other components not shown may also be included within the environment.

Among other components not shown, the system 100 includes a variety of patient care applications, such as applications 102, 104, 106, that can interact with an electronic order management system 108. The patient care applications 102, 104, 106 can be any of a number of different types of healthcare-related solutions that clinicians may employ when diagnosing and treating patients. For instance, the patient care applications 102, 104, 106 can include solutions for emergency rooms, pediatrics, and oncology to name a few.

The electronic order management system 108 can perform the tasks of accepting, validating, scheduling and otherwise processing orders for final implementation. According to embodiments of the invention in one regard, the electronic order management system 108 may be, include or interface to the PowerOrders® platform commercially available from Cerner Corp. Other platforms are possible. Among other things, the electronic order management system 108 may verify that equipment, technicians, laboratory time or other schedules or resources are available to perform entered orders. The electronic order management system 108 may likewise check or validate the clinical propriety of orders, for instance to validate that one test may be safely performed an hour or other scheduled time after another test, or to scan for contraindications to an administered procedure, such as allergies to imaging dyes. In embodiments, the electronic order management system 108 interfaces with computerized solutions for order completion, such as the order fulfillment systems 116, 118. The order fulfillment systems 116, 118 may include, for instance, electronic pharmacy or laboratory management systems.

In one embodiment, the system 100 operates within a comprehensive clinical computing system similar to the exemplary medical information system 700 described below with reference to FIG. 7. By operating within a comprehensive clinical computing system, a number of advantages may be realized. For example, the comprehensive clinical computing system may include computing devices and/or computing systems in a variety of different clinical domains within a healthcare environment. By way of example only and not limitation, the comprehensive clinical computing system may include a clinical laboratory system, a pharmacy system, a radiology system, and a hospital administration system. Accordingly, the comprehensive clinical computing system provides a unified computing architecture that is able to access and aggregate clinical information from a variety of different clinical domains and to make the clinical information available. In an embodiment, the comprehensive clinical computing system may store clinical information from different clinical domains, as well as orders from the electronic order management system 108, in a patient-centric electronic medical record for each patient. The patient-centric electronic medical record may include a comprehensive and current record of all health-care related information available to the healthcare organization for the patient.

As shown in FIG. 1, the electronic order management system 108 includes an order application 110 that allows clinicians to submit orders to the electronic order management system 106. In particular, the order application 110 facilitates the submission of orders via user interfaces for entering orders for patients. The electronic management system 108 also includes an order selection component 112. As will be explained in further detail below, the order selection component 112 operates to automatically select and enter orders into the user interfaces based on diagnoses entered into patient care applications, such as the patient care applications 102, 104, 106.

The order selection component 112 selects orders using a mappings data store 114. The mappings data store 114 includes mappings of one or more types of orders to each of a number of diagnoses available to the system 100. In other words, each mapping corresponds with a diagnosis and identifies one or more types of orders for the diagnosis. In some configurations, a globally unique diagnosis code is used to identify each diagnosis. By using a globally unique diagnosis code for each diagnosis, the system 100 supports the interaction of diverse patient care applications (e.g., applications 102, 104, 106) with the electronic order management system 108. Each of the patient care applications 102, 104, 106, order selection component 112, and mappings data store 114 can use the globally unique diagnosis codes to uniquely identify diagnoses. However, as explained in further detail below, the use of such globally unique diagnosis codes are not required, and the order selection component 112 can be configured to identify mappings for diagnoses from diverse patient care applications that do not support such globally unique diagnosis codes.

Figure 2:
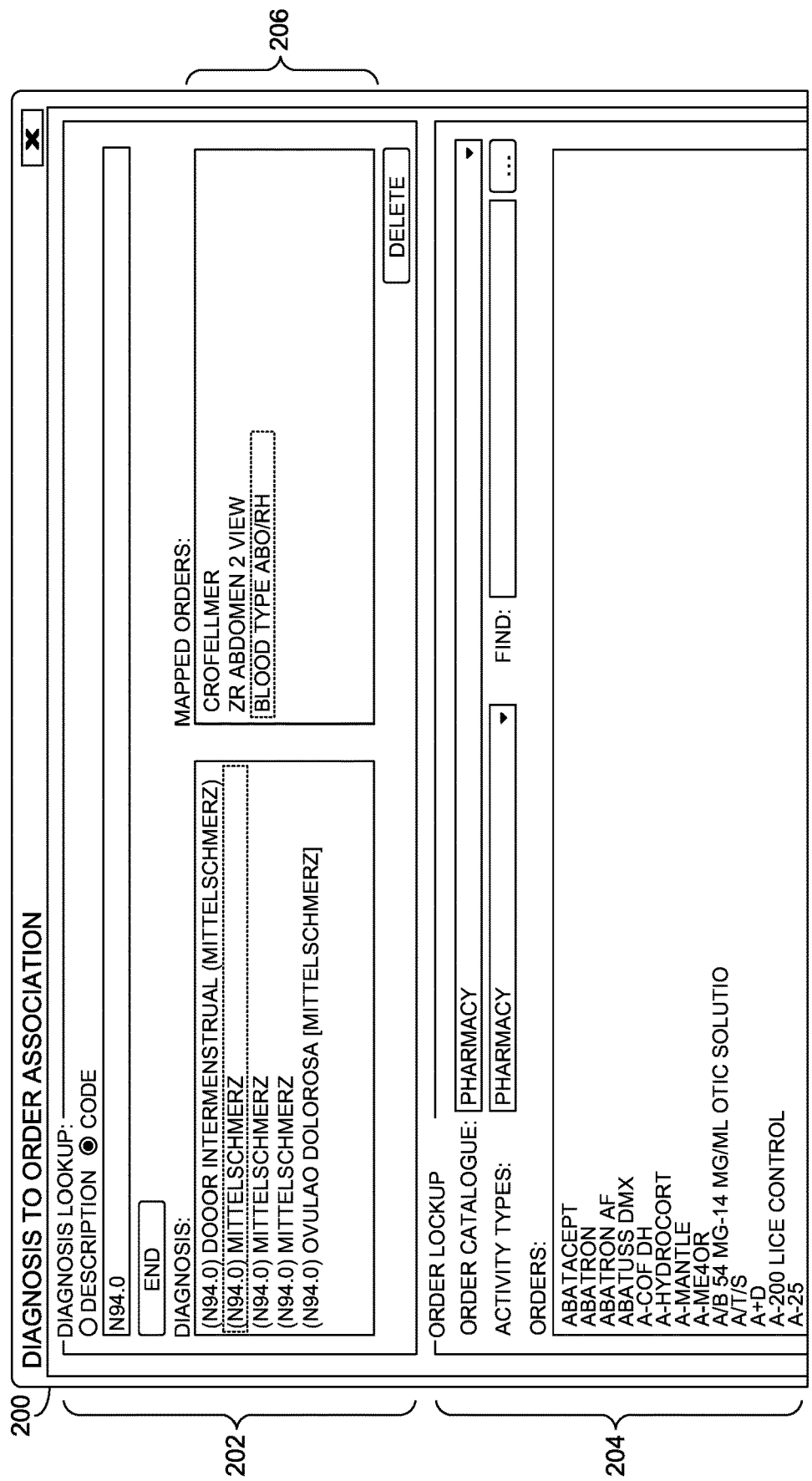
FIG. 2 is a screenshot showing a user interface for mapping orders to diagnoses in accordance with an embodiment of the present invention.

The mapping for each diagnosis in the mappings data store 114 can be generated for instance, using a user interface for associating orders with diagnoses, such as the user interface 200 shown in FIG. 2. The user interface 200 includes a diagnosis selection area 202 for searching diagnoses, for instance, by description or diagnosis code, and selecting a given diagnosis to create a mapping for the diagnosis. All diagnoses coded in the system may be made available for mappings. The user interface 200 also includes an order lookup area 204 for selecting orders. After a diagnosis has been selected in the diagnosis selection area 202, the order lookup area 204 can be used to search and select orders to map to the selected diagnosis. Orders selected for the order lookup area 204 are shown in a mapped order area 206. Once complete, the mapped orders for the selected diagnosis are stored in the mappings data store 114.

In operation, after a diagnosis is entered into a patient care application, such as one of the patient care applications 102, 104, 106, the order selection component 112 determines one or more types of orders for the diagnosis using the mappings data store 114. More particularly, the order selection component 112 can employ a set of rules to select orders as a function of the diagnosis entered into the patient care application. In some configurations, the set of rules can initially include deriving a query that can be used to identifying a mapping for the diagnosis from the mappings data store 114. Because the electronic order management system 108 can interface with diverse patient applications, it's possible that each patient care application can provide different diagnosis information to the order selection component 112. For instance, some patient care applications can be configured to provide a diagnosis code (e.g., a globally unique diagnosis code) that corresponds with the diagnosis codes used by the mapping data store 112, such that a query can be generated based on the provided diagnosis code. In other instance, some patient care application may simply provide text for an entered diagnosis. In such instances, the patient care application can derive a text-based query based on the text provided by the patient care application that is used to query the mapping data store 112. Alternatively, a diagnosis code could be determined based on the text provided by the patient care application by querying a database of diagnosis codes for diagnoses, and the determined diagnosis code could be used to query the mapping data store 112.

After deriving a query, the set of rules used by the order selection component can include querying the mappings data store 114 to identify a mapping for the diagnosis entered into the patient care application and identify, from that mapping, one or more types of orders mapped to the diagnosis. As noted above, in some exemplary configurations, the mappings data store 114 comprises a database keyed on globally unique diagnosis codes. In such configurations, the order selection component 112 may determine the globally unique diagnosis code for the entered diagnosis and use the globally unique diagnosis to identify the mapping (i.e., record) for the diagnosis in the mappings data store 114.

For each type of order identified for the diagnosis, the order selection component 112 inputs an order into a user interface provided for submitting orders via the electronic order management system 108. The user interface can be provided, for instance, by the order application 110 or another application, such as one of the patient care applications 102, 104, 106. In some configurations, the order is generated by retrieving patient data from an electronic medical record for the patient and using the retrieved patient data to populate the order. The user interface with the entered orders is presented to a clinician, who can review the order and determine whether to submit the order for processing via the electronic order management system 108.

Figure 3:
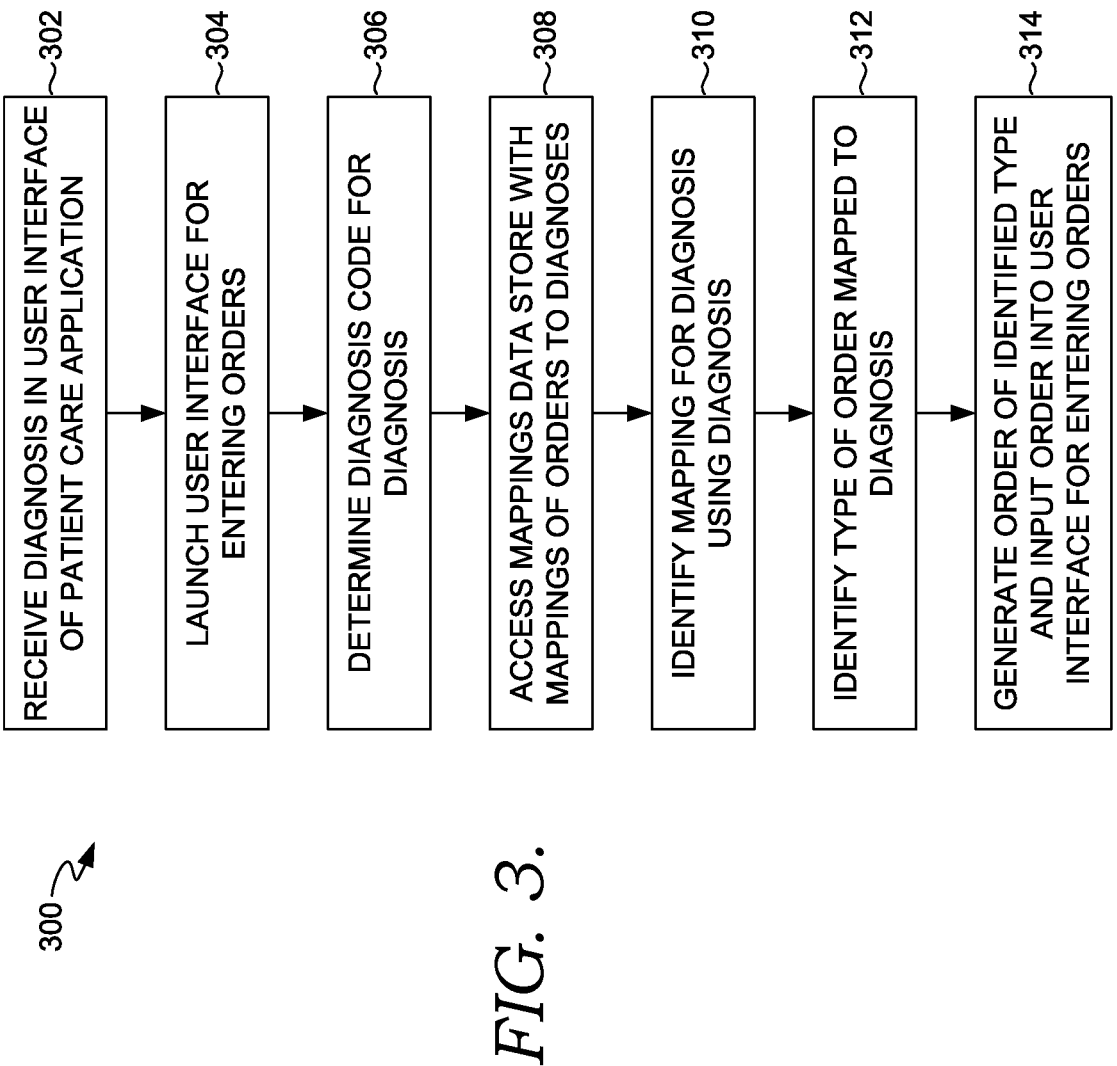
FIG. 3 is a flow diagram showing a method for automatically selecting and entering an order into a user interface for submitting orders based on a diagnosis entered into a patient care application in accordance with an embodiment of the present invention.

Turning now to FIG. 3, a flow diagram is provided showing a method 300 for automatically entering an order into an ordering application based on a diagnosis entered into a patient care application in accordance with some embodiments of the present invention. As shown at block 302, a diagnosis for a patient is received in a user interface provided by a patient care application. The patient care application could be any of a number of different healthcare-related applications (e.g., one of the patient care applications 102, 104, 106 of FIG. 1). The diagnosis could be entered into the patient care application in the course of a typical workflow performed by a clinician. As an example in the context of an emergency care application, when a patient arrives in an emergency department, a clinician may perform an initial assessment and enter a diagnosis for the patient into the emergency care application.

As shown at block 304, a user interface for entering orders for the patient is launched. In some configurations, the user interface is provided by the order application 110 of the electronic order management system 108 of FIG. 1. In other configurations, the user interface is provided by another application, such as the patient care application in which the diagnosis was entered, and the user interface interacts with the order application 110 for submitting orders to the electronic order management system 108.

The user interface for entering orders can be launched in a number of different manners in accordance with various embodiments. In some configurations, the user interface is automatically launched in response to the diagnosis being entered into the patient care application. In other configurations, the user interface is launched in response to a user command. For instance, the patient care application could include a user interface element for launching the user interface. In further configurations, the user interface could be automatically launched based on the typical workflow of the patient care application.

A diagnosis code is determined for the diagnosis, as shown at block 306. In some configurations, the diagnosis code is an identifier that is globally unique for the order application and the patient care applications in which diagnoses can be entered. A data store with mappings of different types of diagnoses to different types of orders is accessed, as shown at block 308. A mapping for the diagnosis is identified at block 310. This may be done, for instance, by using the diagnosis code to identify a mapping with that diagnosis code. A type of order for the diagnosis is identified from the mapping, as shown at block 312. In some instances, multiple types of orders may be mapped to the diagnosis and identified.

An order of the type determined is generated and input into the user interface for entering orders, as shown at block 314. In instances in which multiple types of orders are mapped to the diagnosis, an order for each type of order is generated and input into the user interface. The generation of each order may include retrieving patient data for the patient (e.g., from an electronic medical record for the patient) and populating the order based on the retrieved patient data.

By way of example to illustrate, FIG. 4 provides a screenshot showing a user interface 400 provided by a patient care application that allows for entry of diagnoses for patients. In particular, the user interface 400 is provided by an emergency care application for managing patients being treated by an emergency department. As shown in FIG. 4, the user interface 400 provides a list of patients being treated. Among other things, the user interface 400 allows a clinician to enter a diagnosis for each patient in the form of a "reason for visit" 402. For instance, the clinician has entered "mittelschmerz" as the reason for visit for the patient "Abby Yale" 404.

Figure 5:
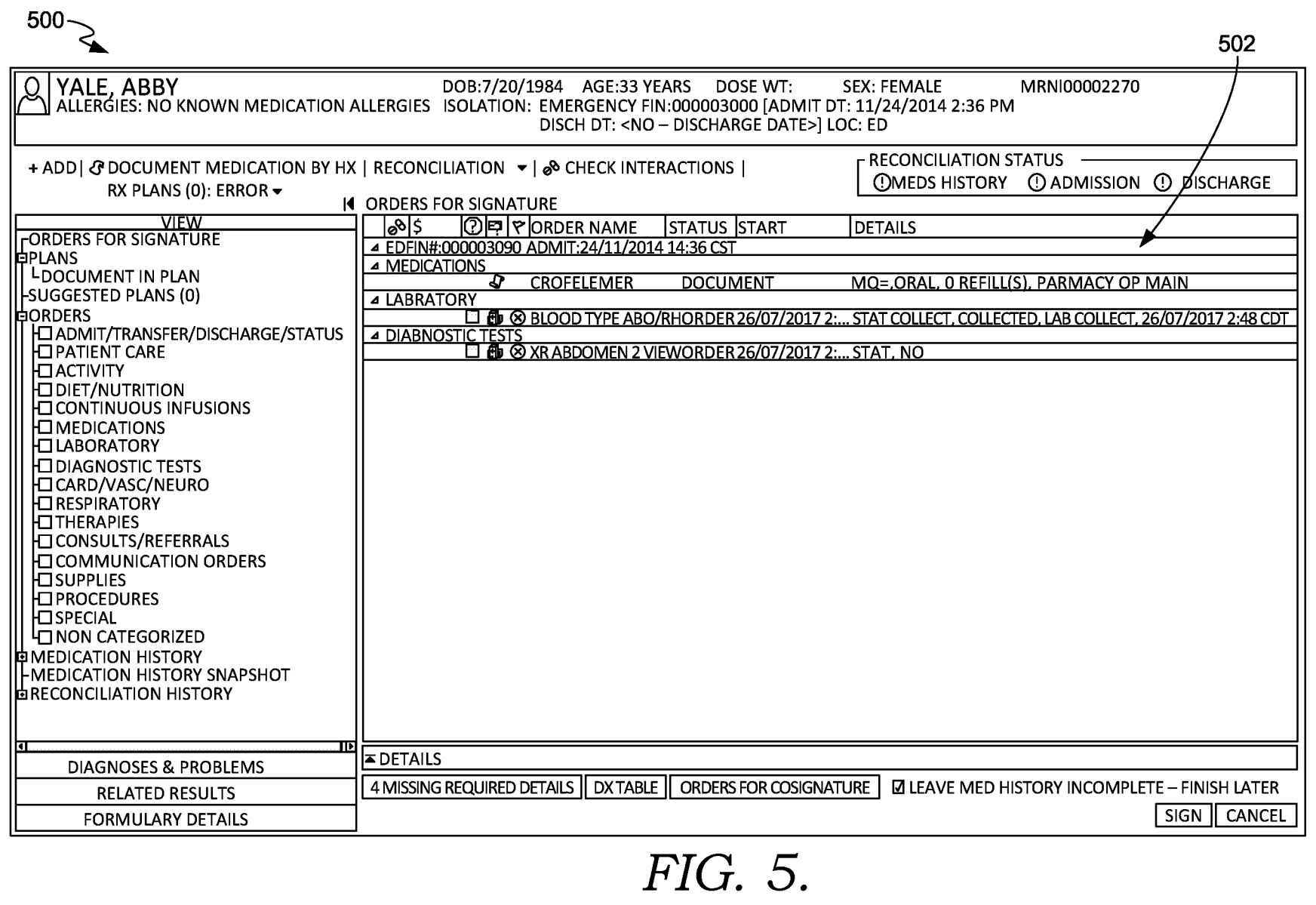

In accordance with the technology described herein, orders can be automatically selected based on the diagnosis entered for a patient into the user interface 400, and the order can be input into a user interface for entering orders via an ordering application. For example, FIG. 5 shows a screenshot of a user interface 500 provided by an ordering application with orders entered for the patient "Abby Yale" selected from the user interface 400 of FIG. 4. As shown in FIG. 5, several orders have been automatically selected by the system and entered into an orders area 502 of the user interface 500. The selected orders included in the user interface 500 are the types of orders that have been mapped to the "mittelschmerz" diagnosis. By employing the user interface 500, a clinician can review the orders and select to submit the orders to the electronic order management system for processing.

As another example, FIG. 6 shows a screenshot of a user interface 600 provided by the emergency care application. The user interface 600 includes an orders area 602 in which orders have been input for the patient "Abby Yale" 404 selected from the user interface 400 of FIG. 4. Again, the orders have been selected based on the types of orders mapped to the "mittelschmerz" diagnosis. If one or more of the orders are selected by the clinician from the orders area 602, the orders are submitted for processing and fulfillment by the electronic order management system via the order application.

Having described embodiments of the present invention, an exemplary operating environment in which embodiments of the present invention may be implemented is described below in order to provide a general context for various aspects of the present invention. The exemplary computing system environment, for instance, a medical information computing system, on which embodiments of the present invention may be implemented is illustrated and designated generally as reference numeral 700 in FIG. 7. It will be understood and appreciated by those of ordinary skill in the art that the illustrated medical information computing system environment 700 is merely an example of one suitable computing environment and is not intended to suggest any limitation as to the scope of use or functionality of the invention. Neither should the medical information computing system environment 700 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

Figure 7:
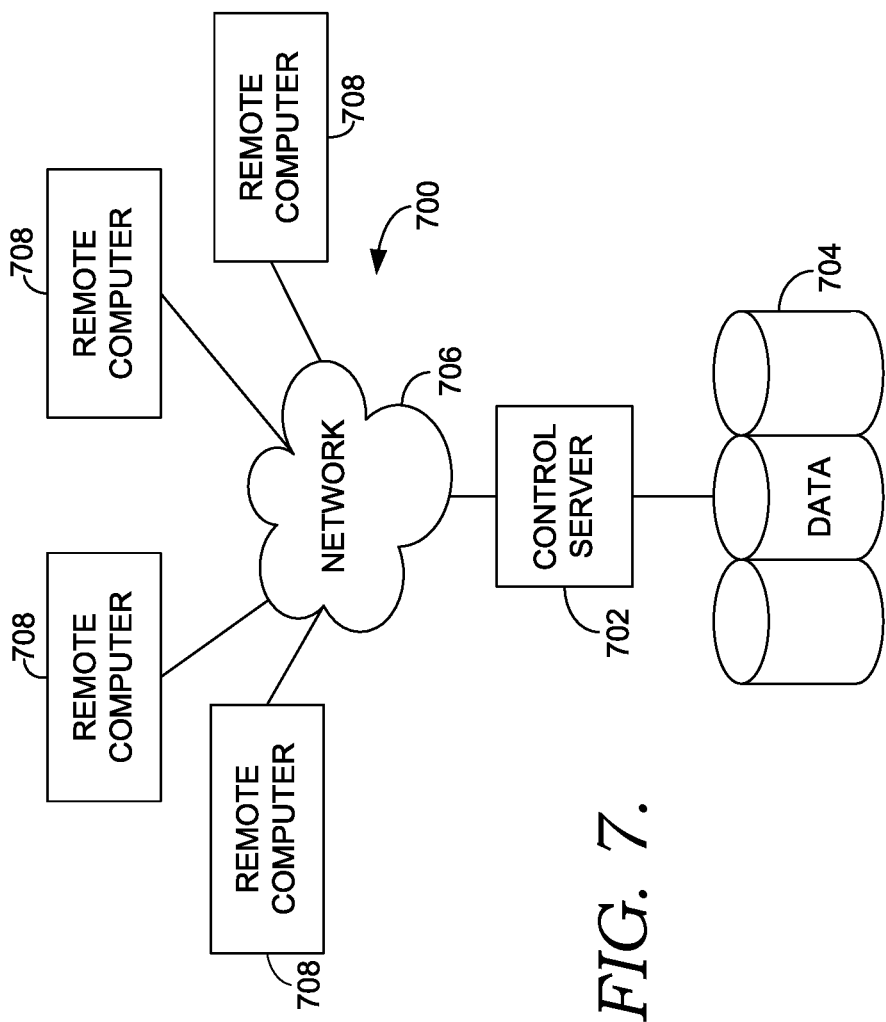
FIG. 7 is a block diagram of an exemplary computing environment suitable for use in implementing the present invention.

With continued reference to FIG. 7, the exemplary medical information computing system environment 700 includes a general purpose computing device in the form of a server 702. Components of the server 702 may include, without limitation, a processing unit, internal system memory, and a suitable system bus for coupling various system components, including database cluster 704, with the server 702. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 702 typically includes, or has access to, a variety of computer readable media, for instance, database cluster 704. Computer readable media can be any available media that may be accessed by server 702, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 702. Computer storage media does not comprise signals per se. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 7, including database cluster 704, provide storage of computer readable instructions, data structures, program modules, and other data for the server 702.

The server 702 may operate in a computer network 706 using logical connections to one or more remote computers 708. Remote computers 708 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, office assistants and the like. The remote computers 708 may also be physically located in non-traditional medical care environments so that the entire health care community may be capable of integration on the network. The remote computers 708 may be personal computers, servers, routers, network PCs, peer devices, other common network nodes, or the like, and may include some or all of the components described above in relation to the server 702. The devices can be personal digital assistants or other like devices.

Exemplary computer networks 706 may include, without limitation, local area networks (LANs) and/or wide area networks (WANs). Such networking environments are commonplace in offices, enterprise-wide computer networks, intranets, and the Internet. When utilized in a WAN networking environment, the server 702 may include a modem or other means for establishing communications over the WAN, such as the Internet. In a networked environment, program modules or portions thereof may be stored in the server 702, in the database cluster 704, or on any of the remote computers 708. For example, and not by way of limitation, various application programs may reside on the memory associated with any one or more of the remote computers 708. It will be appreciated by those of ordinary skill in the art that the network connections shown are exemplary and other means of establishing a communications link between the computers (e.g., server 702 and remote computers 708) may be utilized.

In operation, a user may enter commands and information into the server 702 or convey the commands and information to the server 702 via one or more of the remote computers 708 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 702. In addition to a monitor, the server 702 and/or remote computers 708 may include other peripheral output devices, such as speakers and a printer.

Although many other internal components of the server 702 and the remote computers 708 are not shown, those of ordinary skill in the art will appreciate that such components and their interconnection are well known. Accordingly, additional details concerning the internal construction of the server 702 and the remote computers 708 are not further disclosed herein.

As can be understood, embodiments of the present invention provide a system for detecting anomalous authentication activity in a client-server architecture. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more computer storage media storing computer-useable instructions, that when used by one or more computing devices, cause the one or more computing devices to perform operations comprising:
   receiving, by an electronic order management system from a first patient care application, a first diagnosis for a first patient,
   wherein the first diagnosis is submitted to the first patient care application via a first user interface of the first patient care application,
   wherein receiving the first diagnosis includes receiving a diagnosis code, corresponding to the first diagnosis, from the first patient care application;
   receiving a first set of patient data for the first patient corresponding to the first diagnosis from a first electronic medical record;
   based on the diagnosis code, querying a diagnosis code database comprising diagnosis codes that are each mapped to at least one type of order for at least one diagnosis;
   based on querying the diagnosis code database, determining a first type of order for the first diagnosis corresponding to the diagnosis code;
   causing, by an order application, display of a second user interface for submitting orders, the second user interface comprising:
      the diagnosis code corresponding to the first diagnosis; and
      a first mapped orders section including the first type of order for the first diagnosis corresponding to the diagnosis code;
   based on receiving a first selection of the first type of order at the first mapped orders section displayed via the second user interface, automatically and electronically entering the first type of order for fulfillment via the second user interface, wherein automatically and electronically entering the first type of order for fulfillment includes populating a first order form for the first type of order for fulfillment using the first set of patient data received from the first electronic medical record;

wherein receiving, by the electronic order management system from a second patient care application, a second diagnosis for a second patient, wherein the second diagnosis is submitted to the second patient care application via a third user interface of the second patient care application, wherein receiving the second diagnosis includes receiving text, corresponding to the second diagnosis, from the second patient care application;

receiving a second set of patient data for the second patient corresponding to the second diagnosis from a second electronic medical record;

based on the text corresponding to the second diagnosis, querying a mappings data store to determine a second type of order for the second diagnosis;

causing, by the order application, display of a fourth user interface for submitting orders, the fourth user interface comprising:

the second diagnosis; and a second mapped orders section including the second type of order for the second diagnosis;

based on receiving a second selection of the second type of order at the second mapped orders section displayed via the fourth user interface, automatically and electronically entering the second type of order for fulfillment via the fourth user interface, wherein automatically and electronically entering the second type of order for fulfillment includes populating a second order form for the second type of order for fulfillment using the second set of patient data received from the second electronic medical record.

2. The one or more computer storage media of claim 1, wherein the at least one of the first or second patient care applications is an emergency care application.

3. The one or more computer storage media of claim 1, wherein each of the diagnosis codes is a globally unique diagnosis code, and wherein the diagnosis code database is keyed by globally unique diagnosis codes for a plurality of diagnoses.

4. The one or more computer storage media of claim 1, wherein the second user interface is launched in response to receiving the first diagnosis in the first user interface.

5. The one or more computer storage media of claim 1, wherein the first type of order is a blood test order.

6. The one or more computer storage media of claim 5, wherein the patient data retrieved from the electronic medical record for each of the first patient and the second patient is stored separately from the respective first and second patient care applications.

7. The one or more computer storage media of claim 1, further comprising:

based on querying the diagnosis code database, determining multiple types of orders for the first diagnosis; and receiving a selection of the first type of order, from the multiple types of orders for the first diagnosis, at the first mapped orders section.

8. The one or more computer storage media of claim 1, wherein the operations further comprise transmitting the first type of order and a portion of the patient data to an electronic pharmacy system.

9. The one or more computer storage media of claim 1, wherein the operations further comprise transmitting the first type of order to an order fulfillment system.

10. The one or more computer storage media of claim 1, wherein the patient data comprises patient encounter data and a reason for a patient encounter.

11. The one or more computer storage media of claim 1, where the operations further include:

receiving, by the electronic order management system from a third patient care application, a third diagnosis, wherein the third diagnosis is submitted to the third patient care application via a fifth user interface of the third patient care application, wherein receiving the third diagnosis includes receiving a second text, corresponding to the third diagnosis, from the third patient care application;

receiving a third set of patient data for a third patient corresponding to the third diagnosis from a third electronic medical record;

executing a query, based on the second text corresponding to the third diagnosis, to determine a second diagnosis code corresponding to the third diagnosis;

based on, querying the diagnosis code database, determining a third type of order for the third diagnosis corresponding to the second diagnosis code;

causing, by the order application, display of a sixth user interface for submitting orders, the sixth user interface comprising:

the second diagnosis code corresponding to the third diagnosis;

a third mapped orders section including the third type of order for the third diagnosis corresponding to the second diagnosis code;

based on receiving a third selection of the third type of order at the third mapped orders section displayed via the sixth user interface, automatically and electronically entering the third type of order for fulfillment via the sixth user interface, wherein automatically and electronically entering the third type of order for fulfillment includes populating a third order form for the third type of order for fulfillment using the third set of patient data received from the third electronic medical record.

12. A method of integrating patient care applications with an order application for automatically entering orders for processing by an electronic order management system, the method comprising:

obtaining a first diagnosis entered via a first user interface provided by a first patient care application and a first diagnosis code corresponding with diagnosis codes used by a mapping data store;

querying the mapping data store based on the first diagnosis code, the mapping data store having the diagnosis codes that are each mapped to at least one order for at least one diagnosis;

identifying a first type of order for the first diagnosis by mapping the first diagnosis code to a first order;

displaying, via a second user interface, a mapped orders section for submitting orders, the mapped orders section including the first type of order determined based on querying the mapping data store, the first type of order being selectable for fulfillment via the second user interface;

entering a first order form into the order application via the second user interface for fulfillment of the first type of order for a first patient based on receiving a selection of the first type of order, wherein entering the first order form into the order application includes, retrieving patient data for the first patient from an electronic medical record, and populating the order with the retrieved patient data;

wherein a first order is filled, based on the first order form, for treating the first patient;

obtaining a second diagnosis entered via a third user interface provided by a second patient care application, wherein receiving the second diagnosis includes receiving text, corresponding to the second diagnosis, from the second patient care application;

based on the text corresponding to the second diagnosis, querying the mappings data store to determine a second type of order for the second diagnosis;

displaying, via a fourth user interface, a mapped orders section for submitting orders, the mapped orders section including the second type of order determined based on querying the mapping data store, the second type of order being selectable for fulfillment via the fourth user interface; and entering a second order form into the order application via the fourth user interface for fulfillment of the second type of order for a patient based on receiving a selection of the second type of order, wherein entering the second order form into the order application includes, retrieving patient data for the patient from an electronic medical record, and populating the order with the retrieved patient data, wherein a second order is filled, based on the second order form, for treating the second patient.

13. The method of claim 12, wherein the diagnosis code comprises an identifier that is unique for the patient care application and the ordering application.

14. The method of claim 12, and wherein the first type of order for the first diagnosis is a lab test order or a diagnostic test order, the method further comprising:
receiving details of a sample for the lab test order or a body region for the diagnostic test order; and
automatically populating the second user interface with the details of the sample or the body region.

15. One or more computer storage media storing computer-useable instructions that, when used by one or more computing devices, cause the one or more computing devices to perform operations comprising:
receiving, via a first user interface provided by a first patient care application, a first diagnosis entered for a first patient;
determining a first type of order by:
determining a first globally unique diagnosis code for the first diagnosis;
accessing a data store with a plurality of diagnoses that are each mapped to at least one type of order, wherein each of the plurality of diagnoses has a globally unique diagnosis code and a textual description; and
identifying a first mapping for the first diagnosis in the data store using the first globally unique diagnosis code and the textual description for the diagnosis and determining the first type of order for the diagnosis from the first mapping;
launching, by an order application, a second user interface displaying a mapped orders section for submitting orders, the mapped orders section including the first type of order determined for the diagnosis; and
automatically and electronically transmitting, via the order application, a first order for the first patient based on receiving a selection of the first type of order displayed on the second user interface, wherein automatically entering the first order for the patient includes,
retrieving patient data for the first patient from an electronic medical record; and
populating the first order with the retrieved patient data,
receiving, via a third user interface provided by a second patient care application, a second diagnosis entered for a second patient;
determining a second type of order by:
receiving text, corresponding to the second diagnosis, from the second patient care application;
based on the text corresponding to the second diagnosis, querying a mappings data store to determine a second type of order for the second diagnosis;
identifying a second mapping for the second diagnosis in the mappings data store using the text corresponding to the second diagnosis and determining the second type of order for the diagnosis from the second mapping;
launching, by the order application, a fourth user interface displaying a mapped orders section for submitting orders, the mapped orders section including the second type of order determined for the diagnosis; and
automatically and electronically transmitting, via the order application, a second order for the second patient based on receiving a selection of the second type of order displayed on the fourth user interface, wherein automatically entering the second order for the second patient includes, retrieving patient data for the second patient from an electronic medical record, and
populating the second order with the retrieved patient data.

16. The one or more computer storage media of claim 15, wherein the operations further comprise:
receiving, via a third user interface provided by a third patient care application, a third diagnosis entered for a third patient;
determining a second globally unique diagnosis code for the third diagnosis;
identifying a third mapping for the third diagnosis in the data store using the second globally unique diagnosis code for the third diagnosis and determining a third type of order for the third diagnosis from the third mapping; and
upon launching the order application, automatically entering a third order for the third patient into the order application via the sixth user interface, the third order corresponding to the third type of order.

17. The one or more computer storage media of claim 15, wherein the operations further comprise:
displaying, via the second user interface, an order lookup area comprising a list of orders; and
in response to receiving a selection from the list of orders, populating the mapped orders section with types of orders.

18. The one or more computer storage media of claim 15, wherein the order application is launched in response to receiving the first diagnosis in the first user interface of the first patient care application.

* * * * *